US007692168B2

United States Patent
Moriyama et al.

(10) Patent No.: US 7,692,168 B2
(45) Date of Patent: Apr. 6, 2010

(54) DEVICE AND METHOD FOR OUTPUTTING CHARGED PARTICLE BEAM

(75) Inventors: Kunio Moriyama, Hitachi (JP); Noriaki Ouchi, Tokai (JP); Masahiro Tadokoro, Hitachiohta (JP); Hisataka Fujimaki, Nisshin (JP)

(73) Assignees: Hitachi, Ltd., Tokyo (JP); Hitachi Information & Control Solutions, Ltd., Ibaraki (JP)

( * ) Notice: Subject to any disclaimer, the term of this patent is extended or adjusted under 35 U.S.C. 154(b) by 334 days.

(21) Appl. No.: 11/774,085

(22) Filed: Jul. 6, 2007

(65) Prior Publication Data

US 2008/0067452 A1 Mar. 20, 2008

(30) Foreign Application Priority Data

Jul. 7, 2006 (JP) ............... 2006-187352

(51) Int. Cl.
*A61N 5/10* (2006.01)
(52) U.S. Cl. .................... 250/492.3
(58) Field of Classification Search .......... None
See application file for complete search history.

(56) References Cited

U.S. PATENT DOCUMENTS

| 5,363,008 | A | 11/1994 | Hiramoto et al. |
| 7,301,162 | B2 | 11/2007 | Matsuda et al. |
| 7,385,203 | B2* | 6/2008 | Nakayama et al. ......... 250/400 |
| 7,394,082 | B2* | 7/2008 | Fujimaki et al. ......... 250/492.3 |
| 7,456,415 | B2* | 11/2008 | Yanagisawa et al. ..... 250/492.3 |
| 2004/0200983 | A1* | 10/2004 | Fujimaki et al. ......... 250/492.3 |

FOREIGN PATENT DOCUMENTS

| JP | 2006-141910 | 6/2006 |
| WO | 2006/012452 | 2/2006 |

OTHER PUBLICATIONS

"Monitor unit calculations for range-modulated spread-out Bragg peak fields" by Hanne M Kooy, et al. Phys. Med. Biol. 48 (2003) 2797-2808.
Rev. Sci. Instrum., vol. 64, No. 8, Aug. 1993, pp. 2074-2084.

* cited by examiner

*Primary Examiner*—Jack I Berman
(74) *Attorney, Agent, or Firm*—Mattingly & Malur, P.C.

(57) ABSTRACT

The present invention improves the accuracy of therapy by checking in real time whether an spread-out Bragg peak (SOBP) width agrees with a desired width during irradiation with a beam. The device for outputting a charged particle beam includes a charged particle beam generator 1 including a synchrotron 4; a range modulation device such as a range modulation wheel (RMW) 28 which forms a Bragg peak of an ion beam extracted from this charged particle beam generator 1; an irradiation device 16 which is located in the direction of ion beam propagation of this RMW device 28 and includes a dose monitor 31 for detecting a dose of the ion beam; and an SOBP width calculation device 73 which calculates ion beam Bragg peak formed by the RMW device 28 based on a detection value of the dose monitor 31.

39 Claims, 8 Drawing Sheets

| SOBP WIDTH [cm] | IDEAL DUTY RATIO |
|---|---|
| 1 | 0.415 |
| 2 | 0.504 |
| 3 | 0.577 |
| 4 | 0.636 |
| 5 | 0.684 |
| 6 | 0.724 |
| 7 | 0.758 |
| 8 | 0.788 |
| 9 | 0.814 |
| 10 | 0.839 |
| 11 | 0.863 |
| 12 | 0.887 |
| 13 | 0.910 |
| 14 | 0.934 |
| 15 | 0.957 |
| 16 | 0.979 |

DEVICE AND METHOD FOR OUTPUTTING CHARGED PARTICLE BEAM

BACKGROUND OF THE INVENTION

1. Field of the Invention

The present invention relates to a device and a method for outputting a charged particle beam to treat an affected area of the body by irradiating the affected part of the body with a charged particle beam of, for example, protons and carbon ions.

2. Description of the Related Art

A therapy performed by irradiating an affected part of the body of a cancer patient with a proton, carbon ion, or other charged particle beam (ion beam) is known. A device for outputting a charged particle beam, which is used for this therapy, includes a charged particle beam generator, a beam transport line, and an irradiation device. An ion beam accelerated by the charged particle beam generator reaches the irradiation device located in a rotating gantry through a first beam transport line and then a second beam transport line located in the rotating gantry. The ion beam is outputted from the irradiation device and then applied to an affected part of the patient's body. A synchrotron (circular accelerator) which includes, for example, means for circularly moving a charged particle beam along a circular path, means for resonating betatron vibration of the charged particle beam outside the stability limit of resonance, and an extracting deflector which extracts the charged particle beam from the circular path is known as a charged particle beam generator. An example is described in U.S. Pat. No. 5,363,008, which is hereby incorporated by reference.

In a therapy using an ion beam, for example, when irradiating the affected part of the body with a proton beam, characteristics in which a majority of the proton beam energy is released when proton stops, i.e., when a Bragg peak is formed, are utilized. In this therapy, proton is stopped near the affected part of the body through selection of incident energy of the proton beam so that the majority of the energy (absorbed dose) is applied only to cells of the affected part of the body.

Normally, the affected part of the body has a certain amount of thickness in the depth direction from the body surface of the patient, which is also a direction of ion beam propagation (hereinafter referred to simply as depth direction). In order to effectively irradiate the whole thickness of the affected part of the body in the depth direction with ion beam, it is necessary to control the energy of the ion beam so as to form a flat range of absorbed dose (spread-out Bragg peak hereinafter referred to as SOBP width), which is wide to some extent in the depth direction.

From such a viewpoint, a range modulation device (range modulation wheel hereinafter referred to as RMW) having a plurality of blades whose thickness varies stepwise in circumferential direction, arranged around a rotating shaft has conventionally been advocated to be used (for example, see REVIEW OF SCIENTIFIC INSTRUMENTS VOLUME 64 NUMBER 8 (AUGUST 1993), page 2077, FIG. 30; and PHYSICS IN MEDICINE AND BIOLOGY, VOLUME 48, NUMBER 17 (7 Sep. 2003)). The disclosures of both of these articles are hereby incorporated by reference. The plurality of blades is attached to the rotating shaft. The RMW forms an opening which penetrates between adjacent blades. For example, when the RMW is rotated with the opening positioned at an ion beam path (referred to as beam path), the opening and the blade alternately pass over the beam path. When the ion beam passes the opening, the beam energy does not attenuate and therefore a Bragg peak is produced at the deepest position in the body. When the ion beam passes a thicker portion of the blade, the energy of this ion beam attenuates more and accordingly a Bragg peak is formed at a portion nearer the body surface of the affected part. As the RMW rotates, the position of Bragg peak formation in the depth direction periodically varies. As a result, it is possible to obtain a flat Bragg peak which is comparatively wide in the depth direction of the affected part of the body. Furthermore, it is known that an SOBP width can also be formed with the use of a ridge filter (see REVIEW OF SCIENTIFIC INSTRUMENTS VOLUME 64 NUMBER 8 (AUGUST 1993), page 2078, FIG. 31).

The absorbed dose applied to the affected part of the body can be calculated by measuring a detection value proportional to the absorbed dose by the use of a dose monitor located more upstream than the patient on the axis of ion beam propagation and using a coefficient for converting the detection value into an actual absorbed dose value. It has been proposed that a conversion factor between the detection value by the dose monitor and the absorbed dose value applied to the actual affected part of the body has a correlation between the depth reached by the beam and the SOBP width (for example, in PHYSICS IN MEDICINE AND BIOLOGY VOLUME 48 NUMBER 17 (7 Sep. 2003)).

SUMMARY OF THE INVENTION

An object of the present invention is to provide a device for outputting a charged particle beam, which makes it possible to check whether a spread-out Bragg peak (SOBP) width agrees with a desired width during irradiation with a charged particle beam.

The present invention, for attaining the above-mentioned object, comprises a range modulation device having a thickness varying in a direction of propagation of the charged particle beam to change the energy of the above-mentioned passing charged particle beam so as to form a spread-out Bragg peak in a target to be irradiated; and a spread-out Bragg peak calculation device which calculates spread-out Bragg peak based on a dose detected by a dose detection device located downstream of the range modulation device.

Since the present invention calculates a spread-out Bragg peak based on a dose detected by the dose detection device, it is possible to check whether the spread-out Bragg peak formed in the target to be irradiated agrees with a desired width during irradiation with the charged particle beam.

Preferably, the dose-based calculation of spread-out Bragg peak is performed based on the duty cycle of an output ON/OFF time obtained from a measured dose value.

Thereby, it is possible to obtain an accurate spread-out Bragg peak by calculating the spread-out Bragg peak.

Preferably, it is desirable to provide a spread-out Bragg peak judgment device which determines whether the calculated spread-out Bragg peak agrees with a set width. This makes it easier, based on the judgment result, to check whether the Bragg peak formed in the target to be irradiated agrees with the set width.

It is preferable that, if the calculated spread-out Bragg peak does not agree with the set width, an output of the charged particle beam from the charged particle beam generator be stopped. This improves the accuracy of therapy for the irradiation target using the charged particle beam.

According to the present invention, it is possible to check whether the spread-out Bragg peak agrees with a desired width during irradiation with the charged particle beam.

BRIEF DESCRIPTION OF THE DRAWINGS

Other objects, features and advantages of the invention will become apparent from the following description of embodiments with reference to the accompanying drawings in which.

DETAILED DESCRIPTION OF THE PREFERRED EMBODIMENTS

There is a technology of outputting a charged particle beam while performing on-off control of an output of an ion beam from a synchrotron during rotation of an RMW. With this technology, for example, if passing of the ion beam is allowed for a comparatively long time, i.e., over a wide range of rotational angle of the RMW while rotating the RMW, attenuation of the ion beam largely varies resulting in a wide spread-out Bragg peak (SOBP) width. On the other hand, if passing of the ion beam is allowed for a comparatively short time, i.e., over a narrow range of rotational angle of the RMW while rotating the RMW, attenuation of the ion beam does not vary largely resulting in a narrow SOBP width. By thus performing ON/OFF control of the ion beam output during rotation of the RMW, various SOBP widths can be obtained with a single RMW making it possible to reduce a frequency of replacement of the RMW and smoothly do therapy for many patients.

However, it has turned out that the above-mentioned technology has the following room for further improvements.

Specifically, the technology makes is possible to obtain an SOBP width which best suits an affected part of the patient's body by controlling beam generating operation for each individual patient. However, in order to check whether the SOBP width agrees with a desired value according to the affected part of the patient's body, there has been no other choice but to measure an absorbed dose by entirely absorbing the beam in midstream. Therefore, since a technique for checking the above in real time during irradiation with beam has not yet been established, there has been room for further improvements from the viewpoint of improvement in the accuracy of therapy.

Embodiments of the present invention will be described in details below with reference to the drawings.

First Embodiment

Figure 1:
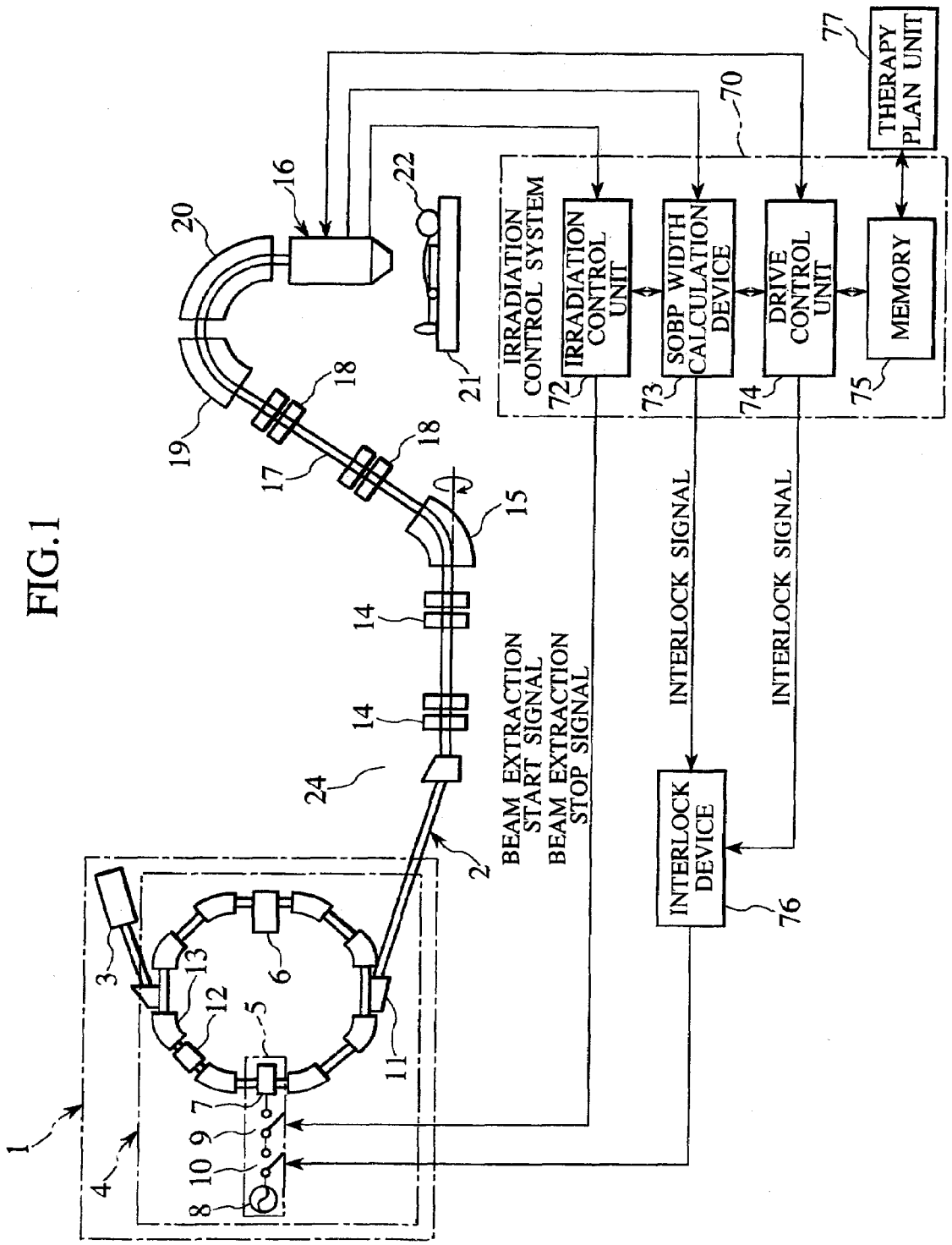
FIG. 1 shows an overall configuration of a device for outputting a charged particle beam according to a first embodiment of the present invention.

A preferred embodiment of a charged particle beam output device according to the present invention will be described below with reference to FIG. 1. A charged particle beam output device 24 according to the present embodiment includes a charged particle beam generator 1, a beam transport line 2 connected to downstream of the charged particle beam generator 1, and an irradiation device (a charged particle beam irradiation device) 16 which is an irradiation apparatus. The charged particle beam output device 24 according to the present embodiment is specifically a proton beam output device.

The charged particle beam generator 1 includes an ion source (not shown), a pre-stage particle accelerator (for example, linear accelerator) 3, and a synchrotron 4 which is a main particle accelerator. In the synchrotron 4, an RF knockout electrode 5, configured with a pair of electrodes, and an RF cavity (accelerator) 6 are located on a circular path of the ion beam. A first RF power supply 8 is connected to the electrode of the RF knockout electrode 5 through switches 9 and 10. A second RF power supply (not shown) which applies RF power is separately prepared in the RF cavity 6. Ion, such as positive ion (or carbon ion), generated in the ion source is accelerated by the pre-stage particle accelerator 3. The ion beam (a charged particle beam) extracted from the pre-stage particle accelerator 3 is injected into the synchrotron 4. The ion beam, which is a charged particle beam, is given energy based on an electromagnetic field generated in the RF cavity 6 by applying the RF power from the second RF power supply, and then accelerated. After being accelerated up to set energy (for example, 100 to 200 MeV), the ion beam circularly moving in the synchrotron 4 is extracted from the synchrotron 4 by closing the switch 9. Specifically, by closing the switch 9, RF power from the first RF power supply 8 is applied to the circularly moving ion beam by the RF knockout electrode 5 through the closed switch 10 and then the switch 9. Therefore, the ion beam circularly moving within a stability limit shifts out of the stability limit and then is extracted through an extracting deflector 11. At the time of ion beam extraction, a current led by a quadrupole magnet 12 and a bending magnet 13 located in the synchrotron 4 is maintained to a set current, and the stability limit is also maintained almost constant. Ion beam extraction from the synchrotron 4 is stopped by opening the switch 9 (or switch 10) to stop application of the RF power to the RF knockout electrode 5.

The ion beam extracted from the synchrotron 4 is transported to a downstream beam path 17 by the beam transport line 2. The beam transport line 2 includes a quadrupole magnet 18 and bending magnets 19 and 20, and is connected to the beam path 17 connecting to an irradiation device 16. The irradiation device 16 and the beam path 17 are attached to a rotating gantry (not shown) located in a therapy room (not shown). The quadrupole magnet 18, the bending magnet 19, and the bending magnet 20 are located on the beam path 17 in this order. The ion beam in the beam path 17 is transported to the irradiation device 16. A patient 22 lies on a treatment bed 21 positioned within a treatment cage (not shown) formed in the rotating gantry. The ion beam outputted from the irradiation device 16 is applied to an affected part of cancer K of the body of the patient 22 (refer to FIG. 2 later mentioned). It can be said that the beam path 17 including the quadrupole magnet 18 or other magnets is also a beam transport line.

Figure 2:
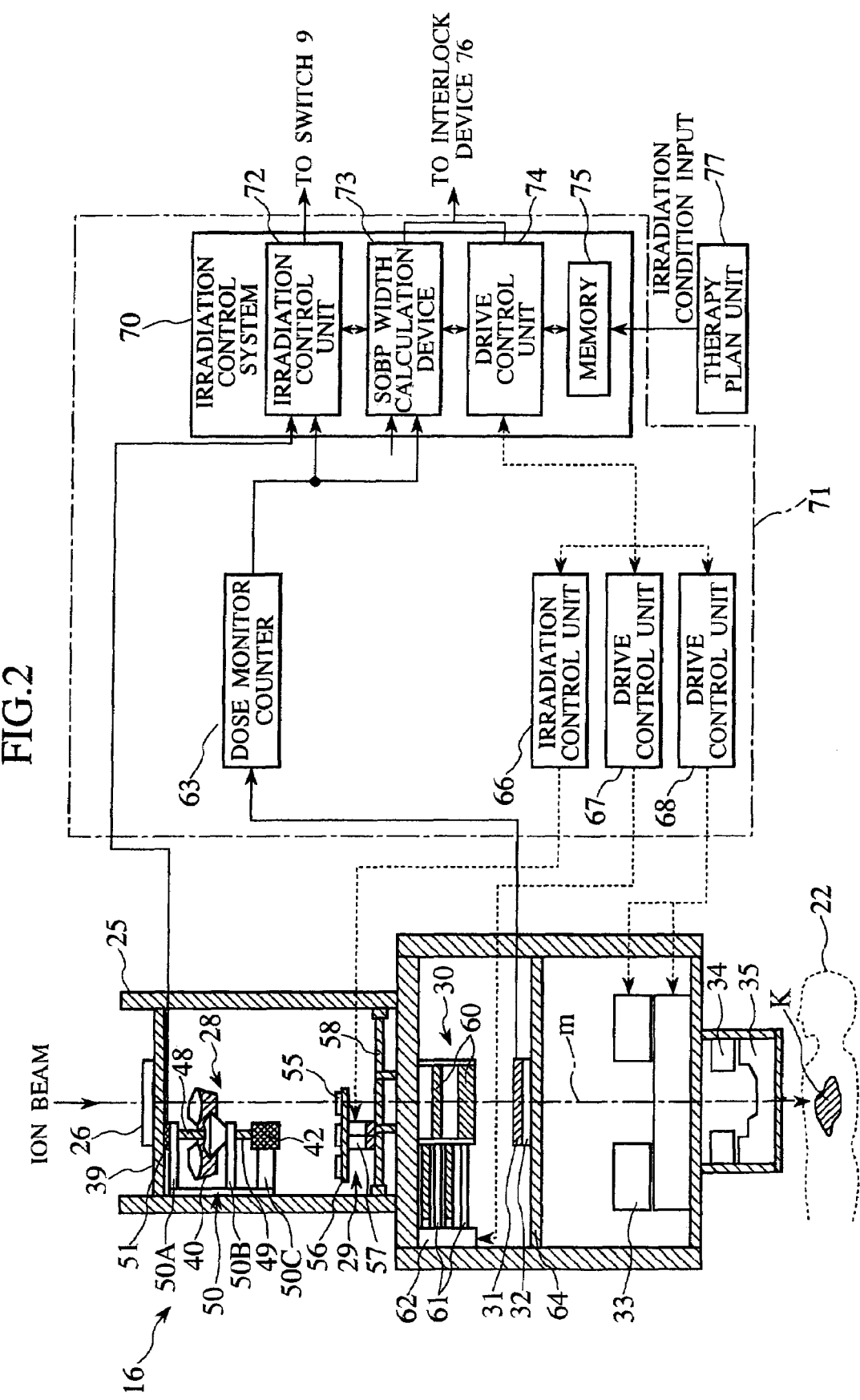
FIG. 2 is a longitudinal sectional view showing a detailed configuration of an irradiation device in FIG. 1.

The structure of the irradiation device 16 will be described below with reference to FIG. 2. As shown in FIG. 2, the irradiation device 16 is attached to the rotating gantry and includes a casing 25 which is connected to the beam path 17.

With the irradiation device 16, a beam profile monitor 26, an RMW device (Bragg peak formation device) 28, a second scatterer 29, a range regulator (for example, a range shifter) 30, a dose monitor 31, a flatness monitor 32, a block collimator 33, a patient collimator 34, and a bolus 35 are arranged on a beam path (beam axis) m in this order from upstream of the direction of ion beam propagation, in the casing 25.

The beam profile monitor 26 is a monitor used to check whether the ion beam injected into the irradiation device 16 from the beam transport line 2 is positioned on the beam axis m. The beam profile monitor 26 is located on a support table 39 attached to the casing 25.

Figure 4:
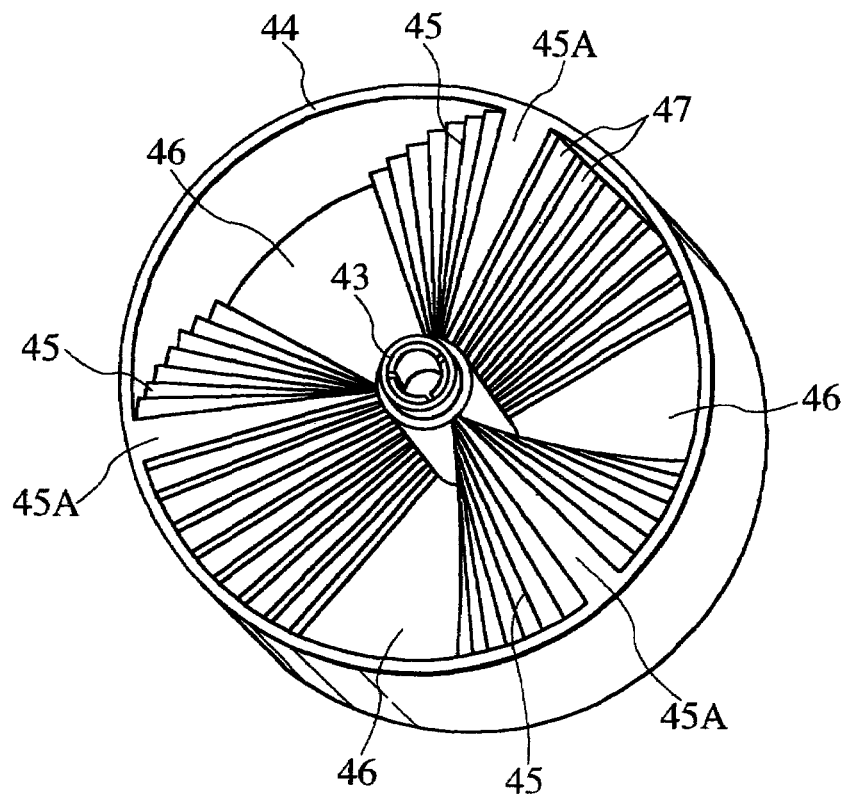
FIG. 4 is a perspective view of an RMW in FIG. 1.

Returning to FIG. 2, the RMW device 28 includes an RMW 40, a rotator (for example, a motor) 42 which rotates the RMW 40, and an angle gauge 51 which detects a rotational angle of the RMW 40. The RMW 40, the rotator 42, and the angle gauge 51 are retained by a support member 50 located in the casing 25. As shown in FIG. 4, the RMW 40 includes a rotating shaft 43, a cylindrical member 44 arranged concentrically with the rotating shaft 43, and a plurality of blades 45 (blades 45A, 45B, and 45C in the present embodiment) attached to the rotating shaft 43, which are extended in the radial direction of the RMW 40, the other end being attached to the cylindrical member 44. These blades 45 are formed so that the circumferential width thereof increases as they are extended from the rotating shaft 43 toward the cylindrical member 44. An opening 46 is formed between the blades 45 in the circumferential direction of the RMW 40. These openings 46 are formed so that the circumferential width thereof increases as they are extended toward the inner side of the cylindrical member 44.

Each blade 45 has a plurality of planar areas (steps) 47 arranged stepwise in the circumferential direction of the RMW 40. The thicknesses between the bottom of the RMW 40 and the planar areas 47 in the shaft direction (direction of the beam axis m) of the rotating shaft 43 differ from each other. Specifically, the level from the bottom of the RMW 40 to the planar areas 47 differ from each other. Here, the thickness relative to a planar area 47 is referred to as the thickness of the planar area. Specifically, with the blade 45, the thickness of each planar area increases stepwise from the opening 46 at both sides of the blade 45 in a circumferential direction toward the planar area 47 positioned at the top having the largest thickness in the direction of the beam axis m. Each planar area 47 is extended from the rotating shaft 43 toward the cylindrical member 44, and the circumferential width also increases as it is extended toward the cylindrical member 44.

The support member 50 located in the casing 25 has supports 50A and 50B facing the direction of the beam axis m and a support 50C located downstream of the support 50B. These supports 50A and 50B respectively allow rotation of rotating shafts 48 and 49. The RMW 40, inserted between supports 50A and 50B, is supported so that the rotating shaft 43 of the RMW 40 is sandwiched by the rotating shafts 48 and 49. Specifically, the rotating shaft 43 is removably attached to the rotating shafts 48 and 49 allowing replacement of the RMW 40. An end of each of the rotating shafts 48 and 49 is inserted into a through-hole prepared on the rotating shaft. The supports 50A and 50B are arranged so that they do not interrupt the beam path in the casing 25. The rotating shafts 43, 48, and 49 are also arranged at positions shifted from the beam path.

The rotator 42 located on the support 50C is connected with the rotating shaft 49. The angle gauge 51 which detects a rotational angle (rotational phase) of the RMW 40 is connected with the rotating shaft 48 and attached to the support 50A. A measured value of a rotational angle of the RMW 40, detected by the angle gauge 51, is inputted to an irradiation control unit 66 of an irradiation control system 70 mentioned later.

In the case of the present embodiment, a first scatterer is located on the beam axis m, between the RMW device 28 and the second scatterer 29 (not shown in FIGS. 2 and 4). This first scatterer is also located in the casing 25. This first scatterer has a function to extend the ion beam that has passed the RMW 40 in a direction perpendicular to the beam axis m.

The second scatterer 29 has a plurality of second scatterers 55, a rotating table 56, and a motor 57. The motor 57 is located on a support member 58 attached to the casing 25. A plurality of second scatterers 55 having different degrees of ion beam scattering are arranged in the circumferential direction on the rotating table 56. When the rotating table 56 is rotated by the motor 57, a predetermined second scatterer 55 is arranged on the beam axis m. Drive of the motor 57 is controlled by a drive control unit 68.

A range regulator 30 includes a plurality of absorbers 60 (four absorbers with the present embodiment) having different thicknesses and an absorber operation device 61 prepared for each absorber 60. An air cylinder driven by compressed air is used as this absorber operation device 61. Each absorber operation device 61 is driven by an absorber drive unit 62 which is controlled by the drive control unit 68.

Figure 3:
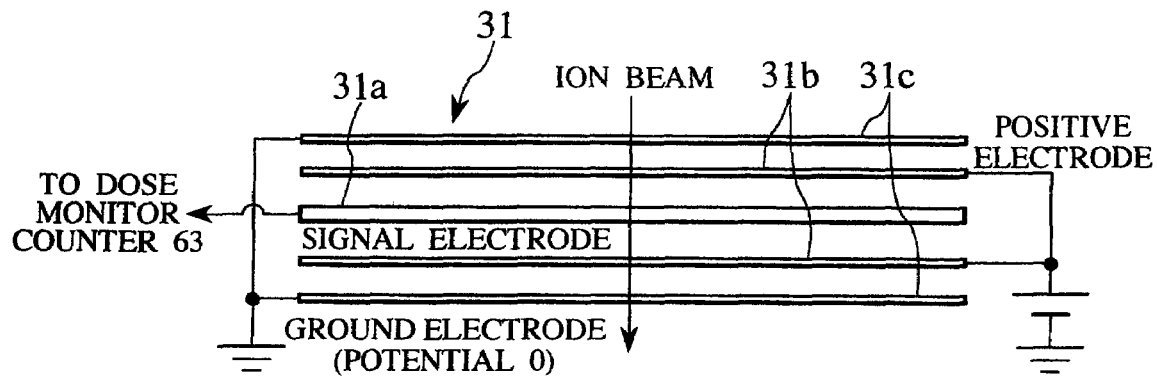
FIG. 3 is a block diagram showing a schematic configuration of a dose monitor in FIG. 1.

The dose monitor 31 is a monitor which measures a dose of an ion beam injected into the irradiation device 16. An example detection principle will be described below with reference to FIG. 3. The dose monitor 31 includes a plurality of overlapped electrode 31a to 31c (for example, five electrodes in this case) which are very thin having a thickness of several micrometers. These five electrodes include a signal electrode 31a located at the center in the direction of ion beam propagation and connected to a dose monitor counter 63; two positive electrodes 31b, to which positive voltage is applied, an which are located so that they sandwich the signal electrode 31a; and two ground electrodes 31c located at outermost positions so that they sandwich these positive electrodes 31b. When the ion beam passes these electrodes, the energy of the beam generates ionized charge between the signal electrode 31a and the positive electrodes 31b and 31b. This ionized charge generated can be taken out from the signal electrode 31a. Since the quantity of ionized charge taken out from the signal electrode 31a is proportional to the dose of the ion beam, the dose of the ion beam can be calculated by counting the quantity of this ionized charge using the dose monitor counter 63. In the case of the present embodiment, a dose measurement device includes the dose monitor 31 and the dose monitor counter 63.

The block collimator 33 shapes the ion beam in the direction of a plane perpendicular to the beam axis m to coarsely collimate the irradiation field of the ion beam. The aperture diameter of the block collimator 33 is variably controlled by the drive control unit 68. The patient collimator 34 is used to collimate the ion beam still more finely according to the shape of an affected part of the body K of the patient 22. The bolus 35 controls the depth reached by the ion beam according to the maximum depth of the affected part of the body K (for example, genesis portion of cancer or tumorous cancer) of the patient 22 under therapy. Also, the bolus 35 controls a range at each position on a plane perpendicular to the beam axis m according to the depth shape of the affected part of the body K which is a target of irradiation.

Returning to FIG. 2, the charged particle beam output device 24 includes an irradiation control system 70. The irradiation control system 70 includes a dose monitor counter 63, an irradiation control unit (second control unit) 72, a spread-out Bragg peak calculation device (hereinafter referred to as SOBP width calculation device) 73, and a drive control unit 74. The SOBP width calculation device 73 is also an SOBP width judgment device. The irradiation control unit 72 performs ON/OFF control of ion beam output from the charged particle beam generator 1 for forming an SOBP width. The SOBP width calculation device 73 calculates an SOBP width of the ion beam being applied and determines whether this SOBP width agrees with a set width. The drive control unit 74 controls the drive of each of the motor 57 of the second scatterer 29, the absorber drive unit 62 of the range regulator 30, and the block collimator 33. Furthermore, the charged particle beam output device 24 includes an interlock device (first control unit) 76.

The thus-configured charged particle beam output device 24 can generate a plurality of SOBP widths by performing ON/OFF control of ion beam output from the charged particle beam generator 1 according to the rotational angle of the RMW 40. This principle will be described below with reference to FIGS. 5, 6, and 7.

When the ion beam passes an opening 46 of the RMW 40, the beam energy does not attenuate and therefore a Bragg peak is formed at a first position deep from the body surface. When the ion beam passes the planar area 47 located at the top 45A having the largest thickness of the blade 45, the beam energy attenuates most and therefore a Bragg peak is formed at a shallow position (a second position) near the body surface. When the ion beam passes the planar area 47 located between the opening 46 and the top 45A, the beam energy attenuates according to the thickness of the portion at which the planar area 47 is located and therefore a Bragg peak is formed at a third position existing between the first and second positions. Therefore, if the beam is always turned ON in 360-degree rotational angle areas in the circumferential direction of the RMW 40, like irradiation condition A in FIGS. 5 and 6, the Bragg peak periodically fluctuates between the first and second positions by the rotation of the RMW 40. As a result, when seen by a time integral, irradiation condition A makes it possible to obtain a comparatively wide SOBP width ranging from a shallow position near the body surface to a deep position like dose distribution A in the depth direction shown in FIG. 7. "Beam ON" means a condition where the ion beam is extracted from the synchrotron 4, passes the RMW 40, and then is outputted from the irradiation device 16. On the other hand, "beam OFF" means a condition where the ion beam is neither extracted from the synchrotron 4 nor outputted from the irradiation device 16.

Figure 5:
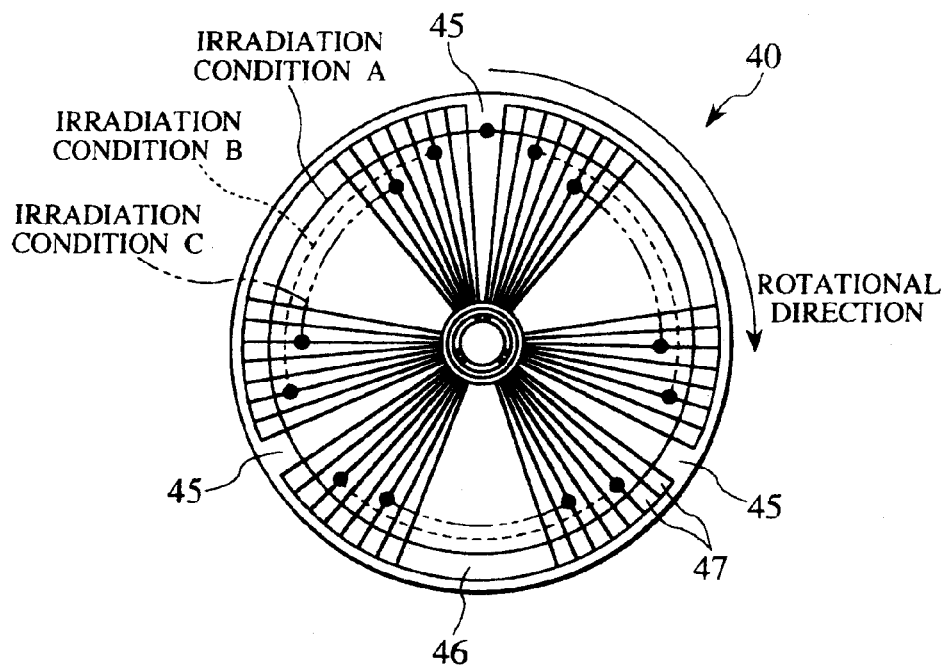
FIG. 5 is a plain view of the RMW in FIG. 4, showing example cases a to c of ion beam output.
Figure 6:
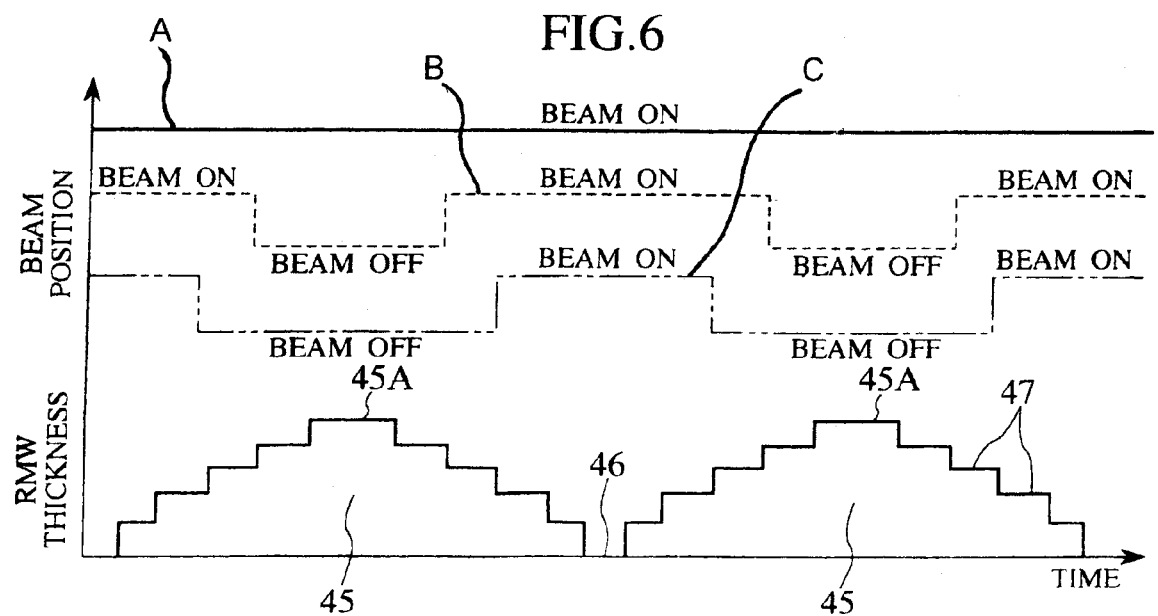
FIG. 6 shows time-series beam ON/OFF sequences for each of cases a to c in FIG. 5.
Figures 7, 8:
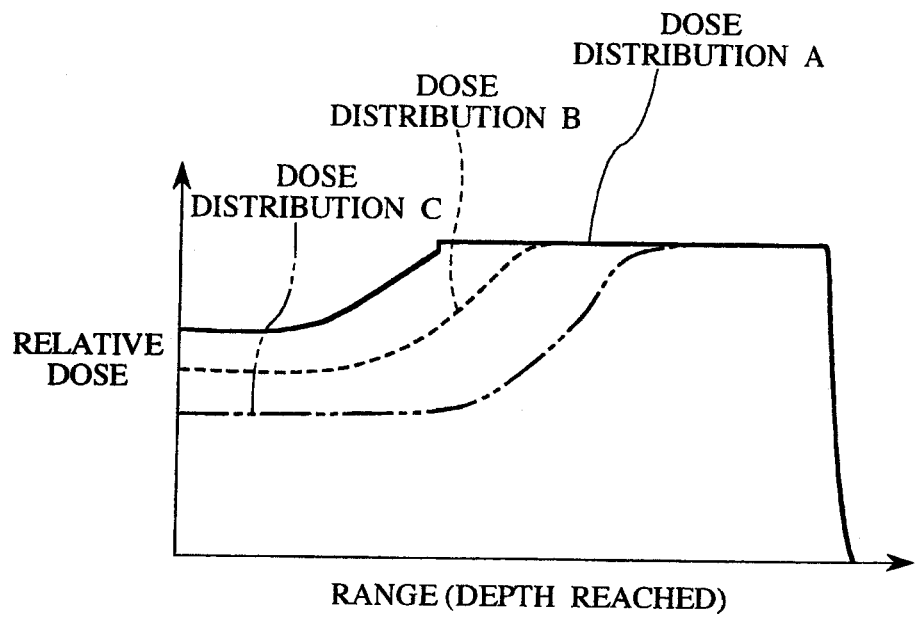
FIG. 7 shows a dose distribution and an SOBP width in the depth direction for each of cases a to c in FIG. 5.
FIG. 8 shows a relationship between an SOBP width and a Duty cycle for a certain RMW.

With irradiation condition B in FIGS. 5 and 6, the beam is turned OFF at comparatively thick areas (near the top) of each blade 45 and turned ON at other rotational angle areas in the circumferential direction of the RMW 40. With irradiation condition B, there is no Bragg peak produced at a shallow portion near the body surface and therefore an SOBP width having dose distribution B in the depth direction shown in FIG. 7 is formed, with a narrower flat portion than dose distribution A.

With irradiation condition C in FIGS. 5 and 6, the beam is turned ON at the opening 46 and at comparatively thin areas of each blade 45 near the opening 46 and turned OFF at other rotational angle areas in the circumferential direction of the RMW 40. With irradiation condition C, the beam energy as a whole attenuates slightly and therefore a Bragg peak is formed at a position deep from the body surface. Therefore, with irradiation condition C, an SOBP width having dose distribution C in the depth direction shown in FIG. 7 is formed, with a narrower flat portion than dose distribution B.

As mentioned above, the charged particle beam output device 24 can form a plurality of SOBP widths with a single RMW by performing ON/OFF control of ion beam output according to the rotational angle of the RMW 40.

It is highly advantageous that various SOBP widths can be formed by performing ON/OFF control of ion beam output during rotation of the RMW 40, as mentioned later. However, in order to improve the accuracy of ion beam therapy, the capability to check whether an SOBP width desired for a certain patient has actually been formed is one of the important requirements for a charged particle beam output device. In order to solve problem, the inventors performed various examinations and determined that an SOBP width formed in the patient's body can be checked during irradiation of the patient with ion beam based on the dose of the ion beam that has passed the RMW device 28. Examination results by these inventors will be described below.

As mentioned above, an SOBP width formed in the patient's body is determined by the output ON/OFF time of the ion beam during rotation of the RMW. Although this relationship is specific for each RMW used, it can be obtained in advance from calculation or experiment results.

As an example, a relationship between an SOBP width and output ON/OFF time for a certain RMW is shown in FIG. 8. The output ON/OFF time is expressed using a duty cycle represented by the following formula, where $T_{ON}$ is output ON time and $T_{OFF}$, output OFF time.

$$\text{Duty} = \frac{Ton}{Ton + Toff} \qquad \text{Formula 1}$$

If a target SOBP width is large, the extraction ON time becomes long accordingly and therefore the duty cycle also becomes large.

In the case of the present embodiment, a set output ON/OFF time corresponding to a target SOBP width for each RMW type is stored in a memory of the irradiation control unit. Therefore, if a target SOBP width is set, an output ON/OFF time is automatically set.

An actually formed SOBP width of ion beam can be calculated by measuring the output ON/OFF time of the ion beam that has passed the RMW and comparing it with the set ON/OFF time. The duty cycle is calculated from the actual ON/OFF time and, with reference to a table of the relationship between the SOBP width and the duty cycle for each RMW calculated in advance (show in FIG. 8), an SOBP width with a matched duty cycle is the actually formed SOBP width of ion beam.

The output ON/OFF time of the ion beam that has actually passed the RMW is calculated using a measurement value of the dose monitor 31 located downstream of the RMW.

Figure 9:
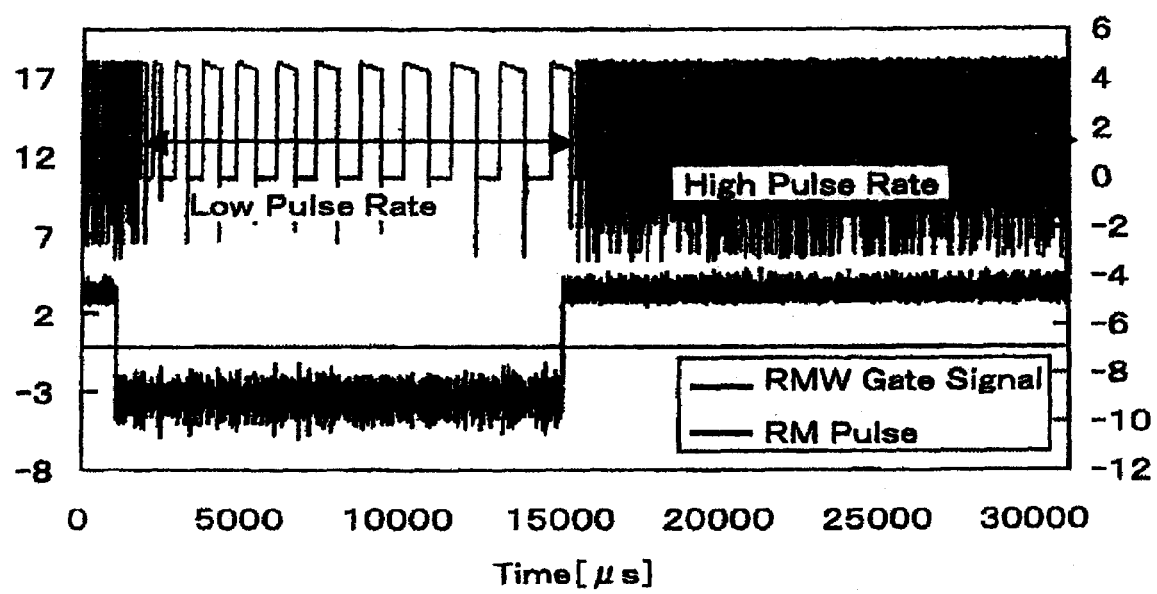
FIG. 9 shows a measurement value pulse signal of a dose monitor when an ion beam output is turned ON and OFF.
Figure 10A:
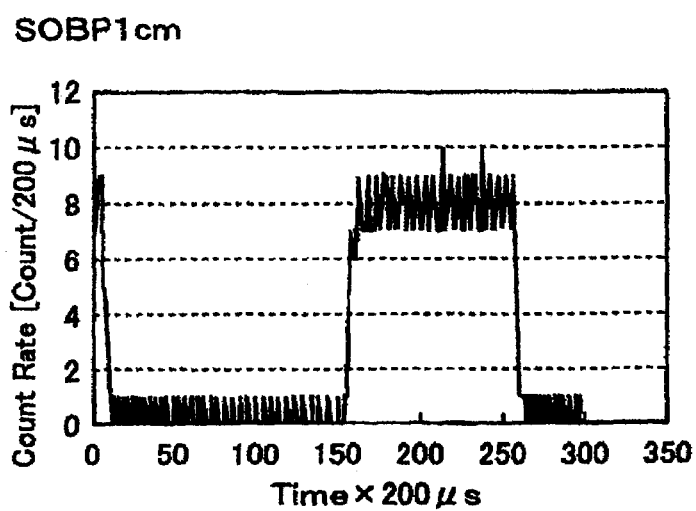
FIGS. 10A-10C show example measurement signals of the dose monitor converted into a count rate per unit time.
Figure 10B:
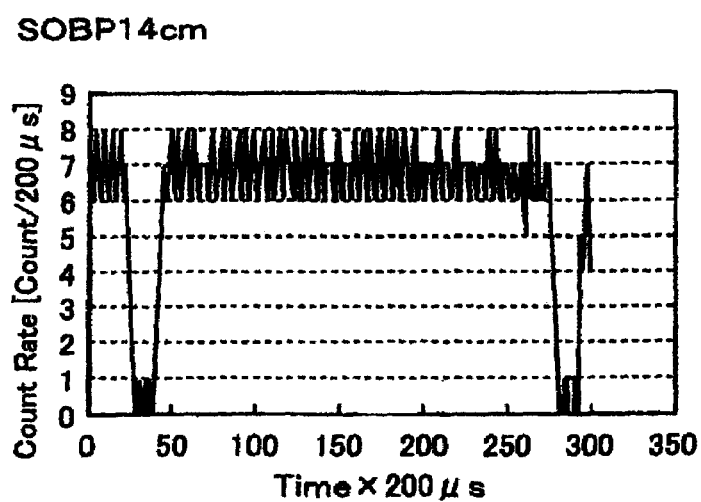
Figure 10C:
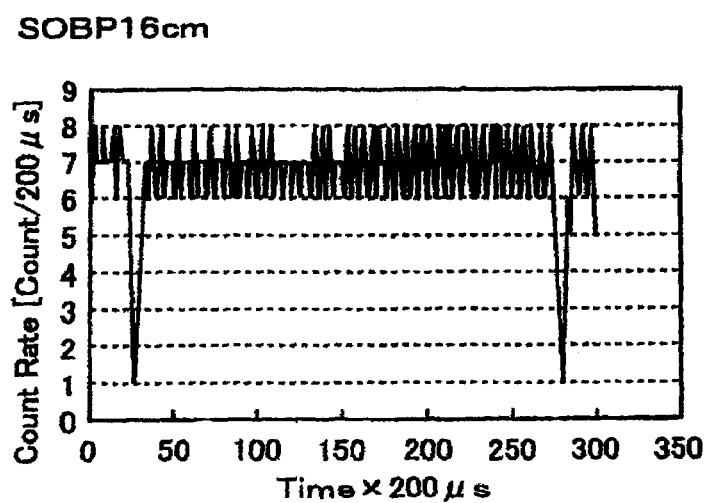

FIG. 9 shows the relationship between the actual output ON/OFF time and the pulse signal outputted from the dose monitor. As mentioned above, the number of charged particles of the ion beam passing the dose monitor increases in proportion to the quantity of outputted beam. Therefore, the number of charged particles of the ion beam passing the dose monitor 31 increases at the timing of output ON, resulting in increased number of pulses inputted to the dose monitor counter 63. Example conversion of the pulse count value of the dose monitor counter 63 into the count rate per unit time is shown in FIGS. 10A-10C.

Although the count value per unit time depends on a unit time setting, it apparently differs according to whether the output is turned ON or OFF, i.e., increases at the time of output ON and decreases at the time of output OFF. In FIGS. 10A-10C, an actual ON/OFF time can be obtained by preparing a threshold value for the count value per unit time, and judging output ON if it is equal to or greater than the threshold value or output OFF if it is equal to or smaller than the threshold value. For the threshold value used for this judgment, it is necessary to select an appropriate value depending on the unit time setting at the time of conversion into a count rate.

In the case of the present embodiment, the conversion of the pulse count value equivalent to the actual amount of ion beam and the threshold value judgment are performed by the SOBP width calculation device. The duty cycle of output ON/OFF obtained by threshold value judgment is compared with the duty cycle corresponding to the set SOBP width previously stored in the memory to make a judgment of the actually formed SOBP width.

The use of this method makes it possible, for example, to perform judgment processing for each rotation according to the rotation of the RMW, and also perform calculation and judgment of the SOBP width formed in the patient's body in real time during irradiation of the affected part of the body with ion beam.

Before starting therapy by the charged particle beam output device 24, a doctor performs diagnosis using a tomogram near the affected part of the body K of the patient 22 obtained by an X-ray CT scanner (not shown) to grasp the position and size of the affected part of the body K; and inputs the irradiation direction of ion beam, a maximum irradiation depth, and other information into a therapy plan unit 77. The therapy plan unit 77 calculates an SOBP width, an irradiation field diameter, a target dose for the patient 22, etc., based on the irradiation direction, the maximum irradiation depth, etc. of the inputted ion beam, using therapy plan software. Furthermore, the therapy plan unit 77 calculates various operation parameters (the energy of the ion beam extracted from the synchrotron 4 (the incident energy to the irradiation device 16), the rotating gantry angle, and the rotational angle of the RMW 40 for irradiation ON/OFF of the ion beam) and at the same time selects an RMW 40 suitable for the therapy. The above-mentioned pieces of therapy plan information, such as the rotational angle and target dose, the irradiation field diameter, the range, the incident energy (incident Eg), the thickness of the first scatterer (SC1 thickness), the SOBP width, the type of the second scatterer 55 (type of SC2), the thickness of an absorber 60 located on the beam path of the range regulator 30 (RS thickness), the aperture diameter of the block collimator 33 (BC aperture diameter), etc. are inputted to a central control unit of the charged particle beam output device and then stored in a memory device (not shown) of the central control unit. Each piece of the above-mentioned therapy plan information is stored in memory of the irradiation control system 70 from the central control unit.

Based on inputted rotating gantry angle information, the gantry control unit (not shown) rotates the rotating gantry so that the beam path of the irradiation device 16 be oriented toward the patient 22 at the angle. The treatment bed 21 on which the patient lies is moved and positioned so that the affected part of the body K be positioned on an extension of the beam path of the irradiation device 16.

The drive control unit 74 of the irradiation control system 70 selects the thickness of the first scatterer, the SOBP width, the type of the second scatterer, the thickness of the absorber, and the aperture diameter of the block collimator from pre-stored irradiation condition information using the stored irradiation field diameter, range, and incident energy. Based on the information of the thickness of the first scatterer, the drive control unit 74 moves the first scatterer of the thickness so that it be positioned on the beam axis m. The drive control unit 74 drives the motor 57 to rotate the rotating table 56 so that the selected second scatterer 55 be positioned on the beam axis m. Furthermore, the drive control unit 68 operates the absorber operation device 61 through the absorber drive unit 62 so that the selected absorber 60 be positioned on the beam axis m. The drive control unit 68 controls a drive unit (not shown) based on the aperture diameter information of the selected block collimator 33, drives each block of the block collimator 33, and sets the aperture diameter to a predetermined diameter.

Various pieces of the therapy plan information are displayed on a display device located in a control room of the charged particle beam output device 24. The RMW 40, the bolus 35, and the patient collimator 34 for the patient 22 under therapy are located in the casing 25 of the irradiation device 16 by workers, as shown in FIG. 2.

The SOBP width calculation device 73 of the irradiation control system 70 reads out from memory related information based on the selected SOBP width and RMW 40 to be used. Furthermore, the irradiation control unit 72 of the irradiation control system 70 reads out from memory the rotational angle information and target dose for the patient 22 under therapy located in the casing 25.

Therapy of the affected part of the body K using the charged particle beam output device 24 will be described below.

The synchrotron 4 is operated by repeatedly causing ion beam to be incident from the pre-stage particle accelerator 3, to be accelerated, to be extracted, and to be decelerated. When the ion beam is accelerated with setup energy to the extraction energy, ion beam acceleration is completed allowing ion beam extraction from the synchrotron 4.

Based on the data read out from memory, the irradiation control unit 72 of the irradiation control system 70 performs judgment of extraction start conditions and then outputs an ion beam extraction ON/OFF command for SOBP width formation. The switch 9 is closed by this extraction ON command. Since the switch 10 is closed, the RF power outputted from the first RF power supply 8 is applied from the RF knockout electrode 5 to the circularly moving ion beam. Then, the ion beam is extracted from the synchrotron 4. This ion beam is transported to the irradiation device 16.

This ion beam advances along the beam axis m within the irradiation device 16. The ion beam passes the beam profile monitor 26 and the rotating RMW 40, and is spread out in a direction perpendicular to the beam axis m by the first scatterer. Then, dose distribution of the ion beam is flattened in a direction perpendicular to the above direction by the second scatterer 55. Then, the ion beam passes the absorber 60 of the range regulator 30 resulting in energy reduction, thus enabling range control within the body of the patient 22. The dose of the ion beam that has passed the absorber 60 is measured by the dose monitor 31, and the flatness in a direction perpendicular to the beam axis m is checked by the flatness monitor 32. The measured dose value is inputted to the dose monitor counter 63. The ion beam further passes the block collimator 33, the patient collimator 34, and the bolus 35, and is applied to the affected part of the body K.

Based on the dose measured by the dose monitor 31, the irradiation control unit 72 constantly determines whether the dose applied to the affected part of the body K has reached the target dose. As a result of judgment, if the dose applied to the affected part of the body K has reached the target dose, the extraction OFF command is outputted, the switch 9 opens, RF power supply to the RF knockout electrode 5 is stopped, and the ion beam extraction from the synchrotron 4 is stopped. This completes irradiation of the patient 22 on the treatment bed 21 with ion beam, thereby stopping the rotation of the rotator 42 and the RMW 40.

The SOBP width calculation device 73 in the irradiation control system 70 determines whether the SOBP width of the ion beam being applied agrees with a predetermined width. Details will be described below.

The quantity of ionized charge equivalent to the dose of the ion beam is detected by the dose monitor 31, counted by the dose monitor counter 63, and inputted to the SOBP width calculation device 73. The SOBP width calculation device 73 converts the inputted pulse value into a count rate per unit time, determines beam ON/OFF time through comparison with a preset threshold value, and calculates the duty cycle (actual result).

The SOBP width calculation device 73 determines whether the calculated duty cycle (actual result) agrees with the duty cycle (setting) obtained from the SOBP width set in the therapy plan information. If the two duty cycles are not in agreement within a certain tolerance, as a result of comparison, the SOBP width calculation device 73 outputs an SOBP width failure signal to an interlock device 76.

At this time, the interlock device 76 outputs an switch OFF signal to the switch 10, and the switch 10 opens. Accordingly, RF power supply from the first RF power supply 8 to the RF knockout electrode 5 is stopped, and ion beam extraction from the synchrotron 4 is stopped. If the duty cycles are in agreement, the SOBP width calculation device 73 outputs an SOBP width normal signal to the interlock device 76, and therefore the interlock device 76 does not output the switch OFF command. Accordingly, irradiation of the patient 22 with ion beam is continued on an assumption that a desired SOBP width has been formed. As mentioned above, this irradiation with ion beam is continued until the dose value obtained from a detection signal of the dose monitor 31 reaches the target dose.

The result of comparison of the duty cycles in the SOBP width calculation device 73 is displayed on a display device 54 as an SOBP width failure or SOBP width normal signal. At this time, an actual SOBP is calculated from a data table (for example, as shown in FIG. 9) which shows the relationship between the duty cycle (actual result) of the actual ion beam output ON/OFF time and the used SOBP width and duty cycle (setting) of the RMW previously stored in memory, and then displayed on the display device 54.

The SOBP width calculation device 73 is also an SOBP width judgment device. The set SOBP width differs for each individual patient 22 and, even with the same patient, differs according to contraction of the affected part of the body K accompanying the progress of therapy.

Since the charged particle beam output device 24 according to the present embodiment performs ON/OFF control of ion beam during rotation of the RMW 40, it is possible to change an area within the RMW 40, over which the ion beam passes, in the rotation direction of the RMW 40. Therefore, it is possible to form a plurality of SOBP widths having different widths in the depth direction from the body surface of the patient 22, allowing one RMW 40 to be used for a plurality of patients. This means that increasing number of patients can be treated using one RMW 40. Furthermore, since a plurality of SOBP widths can be formed using one RMW 40, it is possible to reduce the number of RMWs to be prepared in a cancer therapy center having the charged particle beam output device 24. The ability to form a plurality of SOBP widths with one RMW 40 reduces the number of replacements of the RMW located in the irradiation device 16. This means that the time necessary for preparation of therapy can be shortened resulting in increased number of patients to be treated by the charged particle beam output device 24. In particular, since the present embodiment performs ON/OFF control of ion beam based on the rotational angle (specifically, a measurement value and set value of the rotational angle) of the RMW 40, a specific SOBP width can be formed with a sufficient accuracy. It is possible to form various SOBP widths by changing the rotational angle of the RMW which performs ON/OFF control of the beam.

In the synchrotron 4, the number of ions accelerated remains constant. Therefore, even if the beam ON period is shortened, a current density of the ion beam extracted from the synchrotron 4 during the beam ON period can be increased by increasing the RF power for extraction supplied from the first RF power supply 8 to the RF knockout electrode 5. Accordingly, even if the beam ON period is shortened, it is possible to increase the dose rate (radiation dose applied to a unit volume in unit time) applied to the patient. For the patient 22 having an affected part of the body K with a small thickness or a small volume, the irradiation time of ion beam can be shortened through irradiation with an ion beam having an increased current density. This shortened irradiation time makes it possible to reduce the burden to the patient 22 thereby increasing the number of patients treated per year. Even if the beam ON period is shortened, all ion beams circularly moving can practically be extracted from the synchrotron 4 by increasing the RF power for extraction as mentioned above. Therefore, the degree of radiation of the synchrotron 4 and other apparatuses decreases.

The use of a cyclotron instead of a synchrotron as an accelerator makes it possible to assume a method for leading the ion beam extracted from the cyclotron to the irradiation device 16. However, the cyclotron does not involve a deceleration process unlike the synchrotron and performs the processes for causing ion beam to be incident, accelerated, and extracted in succession. Therefore, if the beam ON period is shortened, the number of ions outputted from the irradiation device 16 per unit time decreases. However, the dose rate with respect to the affected part of the body K remains unchanged. This is equivalent to reduction of the SOBP width, i.e., reduction of the irradiation volume. As a result, even if the beam ON period is shortened, the irradiation time of the ion beam remains unchanged for the patient 22 having an affected part of the body K with a small thickness or a small volume. With the cyclotron, if "beam OFF" is performed during or after the acceleration process of the ion beam, the quantity of ion beam thrown away increases resulting in increased radiation of the cyclotron and other apparatuses.

The charged particle beam output device 24 according to the present embodiment makes it possible to check in real time whether an actual SOBP width formed by beam ON/OFF control for the RMW 40 agrees with the set SOBP width during irradiation with ion beam. If the actual SOBP width does not agree with the set SOBP width, the ion beam extraction can be stopped. Therefore, it is possible to avoid formation of an abnormal SOBP, different from the SOBP set in the therapy plan, within the patient 22. Therefore, the accuracy of therapy by the ion beam has remarkably been improved. Specifically, according to the present embodiment, it is possible to irradiate the patient 22 with ion beam only when an SOBP width set in the therapy plan is formed in the body of the patient 22.

Since an SOBP width failure signal or an SOBP width normal signal outputted from the SOBP width calculation device 73 is displayed on the display device 54, the doctor (or radiation engineer) can check whether an SOBP width formed within the patient 22 is normal or not. Therefore, even if the SOBP width failure signal (SOBP width failure information) is displayed on the display device 54, if ion beam extraction from the synchrotron 4 cannot be stopped because of a failure of the interlock device 76 or the like, the doctor (or radiation engineer) can open the switch 10 by pressing a beam extraction stop button on an operator console (not shown) in the control room. Specifically, it is possible to manually stop ion beam extraction from the synchrotron 4.

Second Embodiment

Figure 11:
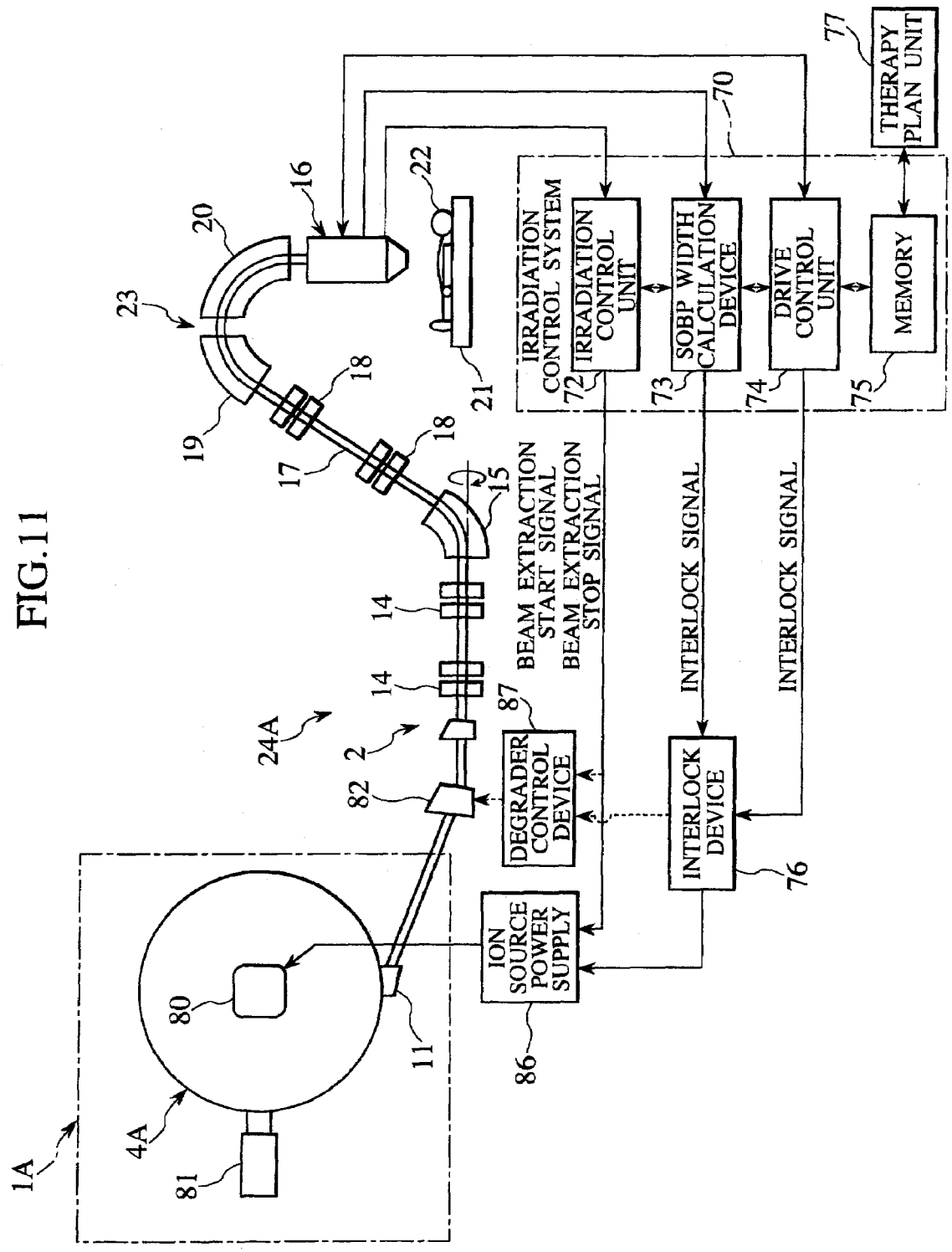
FIG. 11 shows an overall configuration of a device for outputting a charged particle beam according to a second embodiment of the present invention.

Another embodiment of a charged particle beam output device according to the present invention will be described below with reference to FIG. 11. In the case of a charged particle beam output device 24A according to the present embodiment, the charged particle beam generator 1 including the synchrotron 4 in the charged particle beam output device 24 is replaced with a charged particle beam generator 1A including a cyclotron 4A. The charged particle beam output device 24A has a configuration in which an energy changer 82 is added to the beam transport line 2. The irradiation device 16 has an RMW device 28.

The charged particle beam generator 1A includes the cyclotron 4A having an accelerator 81, an ion source 80, and the energy changer 82. The energy changer 82 is located in the beam transport line 2 near the cyclotron 4A. The energy changer 82 includes a plurality of platy degraders over which the ion beam passes to make energy loss, a bending magnet (not shown) which deflects the ion beam that has lost energy, an aperture (not shown) for cutting out a part of the ion beam after passing the bending magnet, and a beam shutter (not shown) which shuts out the transport of the ion beam to downstream of the beam transport line 2.

ON/OFF control of ion beam is performed by the irradiation control unit 72. However, an outputted extraction ON signal is outputted to an ion source power supply. The ion source power supply 86 supplies the power to the ion source 80 by inputting the extraction ON signal. The ion source 80 is activated for extraction of ion beam. This ion beam is injected into the cyclotron 4A and then accelerated by the accelerator 81 up to an energy setting. The ion beam that has been accelerated up to the energy setting is extracted from the cyclotron 4A through the extracting deflector 11. Afterwards, the ion source power supply 86 stops power supply to the ion source 80 by means of an extraction OFF signal outputted from the irradiation control unit 72. Incidence of the ion beam to the cyclotron 4A is stopped, and ion beam extraction from the cyclotron 4A is also stopped.

Furthermore, if the SOBP width calculation device 73 outputs an SOBP width failure signal during ion beam extraction, the interlock device 76 outputs a power supply stop signal to an ion source power supply 87. Power supply from the ion source power supply 86 to the ion source 80 is stopped, and ion beam extraction from the cyclotron 4A is stopped.

The second embodiment makes it possible to obtain effects produced by the first embodiment other than the following two effects obtained by the first embodiment: (1) shortening of the irradiation time of ion beam by applying an ion beam having an increased current density to the patient 22 having an affected part of the body K with a small thickness or a small volume and (2) reduction of radiation degree of apparatuses.

It is also possible to perform ON/OFF control of ion beam not only by activating and deactivating the ion source 80 but also by opening and closing the beam shutter of the energy changer 82. Furthermore, it would be possible to perform ON/OFF control of ion beam incident to the irradiation device 16 by changing the ion beam path by controlling power supply to a bending magnet 15.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A device for outputting a charged particle beam to irradiate the charged particle beam on a target, the device comprising:
    a charged particle beam generator which generates the charged particle beam;
    an irradiation device which includes a range modulation device having a thickness varying in a direction of propagation of the charged particle beam outputted from the charged particle beam generator to change the energy of the passing charged particle beam so that a spread-out Bragg peak is formed in the target to be irradiated, and which outputs the charged particle beam which passed the range modulation device to the target to be irradiated;
    a dose measurement device which measures the dose of the charged particle beam at a position downstream of the range modulation device in the direction of charged particle beam propagation; and
    a spread-out Bragg peak calculation device which calculates a spread-out Bragg peak based on the dose value measured by the dose measurement device.

2. The device for outputting a charged particle beam according to claim 1, the device comprising:
    a spread-out Bragg peak calculation device which performs the dose-based calculation of spread-out Bragg peak based on an output ON/OFF time obtained from the dose value.

3. The device for outputting a charged particle beam according to claim 1, wherein
    the range modulation device has a thickness that varies in a rotational direction of the range modulation device to change the energy of the passing charged particle beam.

4. The device for outputting a charged particle beam according to claim 3, the device comprising:
    a control unit which controls the start and stop of extraction of the charged particle beam from the charged particle beam generator during rotation of the range modulation device.

5. The device for outputting a charged particle beam according to claim 4, the device comprising:
    the control unit which controls the start and stop of extracting of the charged particle beam based on a rotational angle of the range modulation device.

6. The device for outputting a charged particle beam according to claim 1, the device comprising:
    a display device which displays the spread-out Bragg peak.

7. A device for outputting a charged particle beam to irradiate the charged particle beam on a target, the device comprising:
    a charged particle beam generator which generates the charged particle beam;
    an irradiation device which includes a range modulation device having a thickness varying in a direction of propagation of the charged particle beam to change the energy of the passing charged particle beam so as to form a spread-out Bragg peak in the target to be irradiated, and outputs the charged particle beam which passed the range modulation device to the target to be irradiated;

a dose measurement device located downstream of the range modulation device in the direction of charged particle beam propagation; and a spread-out Bragg peak judgment device which calculates a spread-out Bragg peak based on a dose measured by the dose measurement device, and determines whether the calculated spread-out Bragg peak agrees with a set width.

8. The device for outputting a charged particle beam according to claim 7, the device comprising:
a first control unit which controls the charged particle beam generator so that extraction of the charged particle beam is stopped if the calculated spread-out Bragg peak does not agree with the set width.

9. The device for outputting a charged particle beam according to claim 7, the device comprising:
a display device which displays the calculated spread-out Bragg peak.

10. The device for outputting a charged particle beam according to claim 7, the device comprising:
the spread-out Bragg peak calculation device which performs the dose-based calculation of spread-out Bragg peak based on an output ON/OFF time obtained from the dose value.

11. The device for outputting a charged particle beam according to claim 7, wherein
the range modulation device has a thickness that varies in a rotational direction of the range modulation device to change the energy of the passing charged particle beam.

12. The device for outputting a charged particle beam according to claim 11, the device comprising:
a second control unit which controls the start and stop of extraction of the charged particle beam from the charged particle beam generator during rotation of the range modulation device.

13. The device for outputting a charged particle beam according to claim 12, the device comprising:
the second control unit which controls the start and stop of extraction of the charged particle beam based on a rotational angle of the range modulation device.

14. The device for outputting a charged particle beam according to claim 11, wherein
the range modulation device includes a plurality of blades whose thickness varies in the rotational direction to change the energy of the charged particle beam.

15. The device for outputting a charged particle beam according to claim 1, wherein
the charged particle beam generator includes either a synchrotron or a cyclotron.

16. The device for outputting a charged particle beam according to claim 8, the device comprising:
the charged particle beam generator including a synchrotron having an RF knockout electrode; and
the first control unit which stops application of RF power to the RF knockout electrode to stop extraction of the charged particle beam from the synchrotron if the calculated spread-out Bragg peak does not agree with the set width.

17. The device for outputting a charged particle beam according to claim 16, wherein the range modulation device has a thickness that varies in the rotational direction of the range modulation device to change the energy of the passing charged particle beam; and a second control unit which controls the start and stop of extraction of the charged particle beam from the synchrotron during rotation of the range modulation device, wherein the second control unit controls the start and stop of extraction of the charged particle beam by controlling the start and stop of RF power supply to the RF knockout electrode.

18. The device for outputting a charged particle beam according to claim 8, the device comprising:
the charged particle beam generator including a cyclotron and an ion source which inputs the charged particle beam to the cyclotron; and
the first control unit which stops power supply to the ion source to stop extraction of the charged particle beam from the cyclotron if the calculated spread-out Bragg peak does not agree with the set width.

19. The device for outputting a charged particle beam according to claim 8, the device comprising:
the charged particle beam generator including a cyclotron and an ion source which inputs the charged particle beam to the cyclotron;
an energy changer which changes the energy of the charged particle beam extracted from the cyclotron; and
the first control unit which closes a shutter prepared in the energy changer to stop transport of the charged particle beam to the irradiation device if the calculated spread-out Bragg peak does not agree with the set width.

20. A method for outputting a charged particle beam by use of a charged particle beam generator and an irradiation device including a range modulation device, the range modulation device having a thickness varying in a direction of propagation of the charged particle beam extracted from the charged particle beam generator to change the energy of the passing charged particle beam so that a spread-out Bragg peak is formed in the target to be irradiated, the method comprising the steps of:
measuring a dose of the charged particle beam at a position downstream of the range modulation device in the direction of the propagation of the charged particle beam; and
calculating the spread-out Bragg peak based on the dose.

21. The method for outputting a charged particle beam according to claim 20, wherein
the dose-based calculation of spread-out Bragg peak is performed based on an output ON/OFF time obtained from the dose value.

22. The method for outputting a charged particle beam according to claim 20, wherein
when the range modulation device has a thickness varying in a rotational direction of the range modulation device to change the energy of the passing charged particle beam, and is being rotated, extraction of the charged particle beam from the charged particle beam generator is started and stopped.

23. The method for outputting a charged particle beam according to claim 22, wherein
extraction of the charged particle beam is started and stopped based on a rotational angle of the range modulation device.

24. A method for outputting a charged particle beam by use of a charged particle beam generator and an irradiation device including a range modulation device, the range modulation device having a thickness varying in a direction of propagation of the charged particle beam extracted from the charged particle beam generator to change the energy of the passing charged particle beam so that a spread-out Bragg peak is formed in the target to be irradiated, the method comprising the steps of:

measuring a dose of the charged particle beam at a position downstream of the range modulation device in the direction of the propagation of the charged particle beam; and calculating the spread-out Bragg peak based on the dose and determine whether the calculated spread-out Bragg peak agrees with a set width.

25. The method for outputting a charged particle beam according to claim 24, wherein extraction of the charged particle beam is stopped if the calculated spread-out Bragg peak does not agree with the width setting.

26. The method for outputting a charged particle beam according to claim 24, wherein the calculated spread-out Bragg peak is displayed on a display device.

27. The method for outputting a charged particle beam according to claim 24, wherein the dose-based calculation of spread-out Bragg peak is performed based on a dose rate per unit time of a value of the dose.

28. The method for outputting a charged particle beam according to claim 24, wherein when the range modulation device has a thickness that varies in the rotational direction to change the energy of the passing charged particle beam, and is being rotated, extraction of the charged particle beam from the charged particle beam generator is started and stopped.

29. The method for outputting a charged particle beam according to claim 28, wherein extraction of the charged particle beam is started and stopped based on a rotational angle of the range modulation device.

30. A device for outputting a charged particle beam to irradiate the charged particle beam on a target, the device comprising:

a charged particle beam generator which generates the charged particle beam;

an irradiation device having a range modulation device which outputs the charged particle beam, which has passed through the range modulation device, to the target to be irradiated;

a time calculation device which calculates a time when the charged particle beam passes the range modulation wheel; and a spread-out Bragg peak calculation device which calculates a spread-out Bragg peak width based on the time when the charged particle beam passes the range modulation device calculated by the time calculation device.

31. The device for outputting a charged particle beam according to claim 30, wherein the time calculation device includes a dose measurement device which measures a dose value of the charged particle beam at a position downstream of the range modulation device in a direction of charged particle beam propagation, and wherein the time when the charged particle beam passes the range modulation device is calculated based on the dose value measured by the dose measurement device.

32. The device for outputting a charged particle beam according to claim 30, wherein the spread-out Bragg peak calculation device calculates the spread-out Bragg peak width based on a duty cycle according to the following formula:

duty cycle=$T_{ON}/(T_{ON}+T_{OFF})$ wherein $T_{ON}$ represents the time when the charged particle beam passes the range modulation device calculated by the time calculation device, and $T_{OFF}$ represents the time when the charged particle beam does not pass the range modulation device.

33. The device of claim 30, wherein the range modulation device has a thickness varying in a direction of propagation of the charged particle beam outputted from the charged particle beam generator to change the energy of the passing charged particle beam so that the spread-out Bragg peak is formed in the target to be irradiated.

34. A method for outputting a charged particle beam by use of a charged particle beam generator and an irradiation device including a range modulation device, the method comprising the steps of:

calculating a time when the charged particle beam passes the range modulation device; and calculating a spread-out Bragg peak width based on the time when the charged particle beam passes the beam energy moderator.

35. The method for outputting a charged particle beam according to claim 34, wherein the time when the charged particle beam passes the range modulation device is calculated based on a dose value of the charged particle beam measured at a position downstream of the range modulation device in a direction of charged particle beam propagation.

36. The method for outputting a charged particle beam according to claim 34, wherein the spread-out Bragg peak width is calculated by a duty cycle according to the following formula:

duty cycle=$T_{ON}/(T_{ON}+T_{OFF})$ wherein $T_{ON}$ represents the time when the charged particle beam passes the range modulation device calculated by the time calculation device, and $T_{OFF}$ represents the time when the charged particle beam does not pass the range modulation device.

37. The method according to claim 34, wherein the range modulation device has a thickness varying in a direction of propagation of the charged particle beam extracted from the charged particle beam generator to change the energy of the passing charged particle beam so that a spread-out Bragg peak is formed in the target to be irradiated.

38. The method according to claim 34, further comprising the steps of:

comparing the calculated spread-out Bragg peak with a preset spread-out Bragg peak that is previously determined for the target; and determining, based upon the result of the comparing step, whether or not the calculated spread-out Bragg peak is appropriate for the target.

39. The method according to claim 34, further comprising the steps of:

comparing the calculated spread-out Bragg peak with a preset spread-out Bragg peak that is previously determined for the target; and outputting the result of comparing step so that it can be determined whether or not the calculated spread-out Bragg peak is appropriate for the target.

* * * * *